US009308295B2

(12) United States Patent
Carter et al.

(10) Patent No.: US 9,308,295 B2
(45) Date of Patent: *Apr. 12, 2016

(54) OXYGENATED DEMINERALIZED BONE MATRIX FOR BONE GROWTH

(71) Applicant: THERACELL, INC., Northridge, CA (US)

(72) Inventors: Andrew J. Carter, Stow, MA (US); Nelson L. Scarborough, Andover, MA (US); Richard K. Grant, Scottsdale, AZ (US); Frank M. Phillips, Highland Park, IL (US); Stephen H. Hochschuler, Paradise Valley, AZ (US)

(73) Assignee: THERACELL, INC., Northridge, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/485,376

(22) Filed: Sep. 12, 2014

(65) Prior Publication Data

US 2015/0004247 A1    Jan. 1, 2015

Related U.S. Application Data

(63) Continuation of application No. 13/740,244, filed on Jan. 13, 2013, now Pat. No. 8,859,007.

(51) Int. Cl.
| | | |
|---|---|---|
| A61K 35/32 | (2015.01) | |
| A61F 2/00 | (2006.01) | |
| A01N 59/26 | (2006.01) | |
| A61K 33/42 | (2006.01) | |
| A01N 59/10 | (2006.01) | |
| A61K 33/14 | (2006.01) | |
| C04B 12/04 | (2006.01) | |
| C04B 28/26 | (2006.01) | |
| A61L 27/36 | (2006.01) | |
| A61L 27/50 | (2006.01) | |

(52) U.S. Cl.
CPC ............. *A61L 27/3608* (2013.01); *A61L 27/50* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 2003/0039678 A1* | 2/2003 | Stone et al. .................... | 424/424 |
| 2003/0190367 A1 | 10/2003 | Balding | |
| 2005/0177247 A1 | 8/2005 | Canham et al. | |
| 2006/0205652 A1* | 9/2006 | Zamora et al. .................. | 514/12 |
| 2006/0222587 A1 | 10/2006 | Prasad et al. | |
| 2008/0175825 A1* | 7/2008 | Hampson et al. ............ | 424/93.7 |
| 2009/0017092 A1 | 1/2009 | Dutta et al. | |
| 2009/0214649 A1 | 8/2009 | Gazit et al. | |
| 2009/0226523 A1 | 9/2009 | Behnam et al. | |
| 2009/0238758 A1 | 9/2009 | Wellisz et al. | |
| 2011/0271957 A1 | 11/2011 | Matis et al. | |
| 2012/0082704 A1 | 4/2012 | Phillips et al. | |
| 2012/0230966 A1 | 9/2012 | Crawford et al. | |

OTHER PUBLICATIONS

Cammisa, Frank P. et al.; "Two-Year Fusion Rate Equivalency Between Grafton® DBM Gel and Autograft in Posterolateral Spine Fusion"; Spine; vol. 29; No. 6; 2004; pp. 660-666.
Clark, Leland C. et al.; "Recent Advances in the Preparation and Use of Perfluorodecalin Emulsions for Tissue Perfusion"; Oxygen Transport to Tissue: Pharmacology, Mathematical Studies, and Neonatology; Adv. Exp. Med. Biol.; V. 37A-B; pp.687-692, 1973.
Clark, Leland C. et al.; "Emulsions of perfluorinated solvents for intravascular gas transport [1,2]"; Fed. Proc.; vol. 34; No. 6; May 1975; pp. 1468-1477.
Gomes, Ligia et al.; "Perfluorocarbon Compounds Used As Oxygen Carriers: From Liquid Ventilation to Blood Substitutes"; 2007; 8pp.
Helm, Gregory A. et al.; "Bone graft substitutes for the promotion of spinal arthrodesis"; Neurosurg Focus; 10(4); Article 4; 2001; 5pp.
Helm, Gregory A. et al.; "Gene-based therapies for the induction of spinal fusion"; Neurosurg Focus; 10(4); Article 5; 2001; 5pp.
Kalfas, Iain H. et al.; "Principles of bone healing"; Neurosurg Focus; 10(4); Article 1; 2001; 4pp.
Kang, Q. et al., "Characterization of the distinct orthotopic bone-forming activity of 14 BMPs using recombinant adenovirus-mediated gene delivery"; Gene Therapy; 2004; 11; pp. 1312-1320.
Keipert, Peter E.; "Oxygent™, A Perfluorochemical-Based Oxygen Therapeutic for Surgical Patients"; Blood Substitutes; Chapter 28; 2006; pp. 312-323.
Keipert, Peter E.; "Use of Oxygent™, A Perfluorochemical-Based Oxygen Carrier, As An Alternative to Intraoperative Blood Transfusion"; Art. Cells, Blood Subs., and Immob. Biotech.; 23(3); 1995; pp. 381-394.
Khan, Safdar N. et al.; "Use of Osteopromotive Growth Factors, Demineralized Bone Matrix, and Ceramics to Enhance Spinal Fusion"; J. Am Acad. Orthop. Surg.; 13; 2005; pp. 129-137.
Khattak, Sarwat F. et al.; "Enhancing Oxygen Tension and Cellular Function in Alginate Cell Encapsulation Devices Through the Use of Perfluorocarbons"; Biotechnol. And Bioeng.; vol. 96; No. 1; Jan. 1, 2007; pp. 156-166.
Kimelman-Bleich, Nadav et al.; "The use of a synthetic oxygen carrier-enriched hydrogel to enhance mesenchymal stem cell-based bone formation in vivo"; Biomaterials; 30; 2009; pp. 4639-4648.
Louis-Ugbo, John et al.; "Evidence of Osteoinduction by Grafton Demineralized Bone Matrix in Nonhuman Primate Spinal Fusion"; Spine; vol. 29; No. 4; 2004; pp. 360-366.

(Continued)

*Primary Examiner* — Chris R Tate
*Assistant Examiner* — Douglas F White
(74) *Attorney, Agent, or Firm* — Lewis Roca Rothgerber Christie LLP

(57) ABSTRACT

An improved composition for inducing bone growth is provided that is a mixture of DBM and a perfluorocarbon oxygen carrier. Injection/implantation of a composition of DBM and a perfluorocarbon results in enhancement of bone formation.

19 Claims, 2 Drawing Sheets

(56) References Cited

OTHER PUBLICATIONS

Martin, George J. et al.; "New Formulations of Demineralized Bone Matrix as a More Effective Graft Alternative in Experimental Posterolateral Lumbar Spine Arthrodesis"; Spine; vol. 24; No. 7; 1999; pp. 637-645.

Peterson, Brett et al.; "Osteoinductivity of Commercially Available Demineralized Bone Matrix"; J. of Bone and Joint Surg.; vol. 86-A; No. 10; Oct. 2004; pp. 2243-2250.

Sassard, Walter R. et al.; "Augmenting Local Bone With Grafton Demineralized Bone Matrix for Posterolateral Lumbar Spine Fusion: Avoiding Second Site Autologous Bone Harvest"; Orthopedics; vol. 23; No. 10; Oct. 2000; pp. 1059-1065.

Subach, Brian R. et al.; "Bone morphogenetic protein in spinal fusion: overview and clinical update"; Neurosurg. Focus; 10(4); Article 3; 2001; 6pp.

* cited by examiner

OXYGENATED DEMINERALIZED BONE MATRIX FOR BONE GROWTH

CROSS-REFERENCE TO RELATED APPLICATION(S)

This application is a continuation of U.S. patent application Ser. No. 13/740,244, filed Jan. 13, 2013, the entire contents of which are incorporated herein by reference.

BACKGROUND

Bone grafting, in the field of orthopedics, refers to natural or synthetic bones transplanted into the diseased or damaged site to help promote re-generation of new bone. The efficacy of bone grafts is based on at least three concepts: osteogenesis, osteoinduction, and osteoconduction. Osteogenesis is defined as the ability to produce new bone, and is determined by the presence of osteoprogenitor cells and osteogenic precursor cells in the area. Both fresh autografts and bone marrow cells contain osteogenic cells, although often in decreased numbers in the elderly patient (Helm G A, Dayoub H, and Jane J A Jr, Neurosurg Focus, 10(4), E5, 2001).

Osteoconduction is defined as the ability of bone to grow on a surface or structure. Osteoconductive properties may be determined by the presence of a structure (scaffold) that allows for vascular and cellular migration, attachment, and distribution (Helm G A, Dayoub H, and Jane J A Jr, Neurosurg Focus, 10(4), E4, 2001). These osteoconductive properties may be altered by structure, pore size, and porosity of the scaffold. (Helm et al., Neurosurg Focus, 10(4), E4, 2001.) Osteoconduction may be achieved through the use of autografts, allografts, DBM (demineralized bone matrix), hydroxyapatite, and collagen. Osteoinduction is defined as the ability to stimulate stem cells to differentiate into mature bone forming cells through stimulation by local growth factors (Subach B R, Haid R W, Rodts G E, et al., Neurosurg Focus, 10(4):Article 3, 2001). Bone morphogenetic proteins and DBM are the most potent osteoinductive materials, although allo- and autografts have some osteoinductive properties (Kalfas I H, Neurosurg Focus 10(4), E1, 2001). Improving the processing and administration of an oxygenated DBM composition will improve the osteogenesis, osteoconduction, and osteoinduction capabilities in bone grafting to advance the state of the art in bone repair.

SUMMARY

In some embodiments of the present invention, a composition includes demineralized bone matrix and a perfluorocarbon. In some embodiments, the perfluorocarbon is perfluorodecalin, perfluorohexane, perfluorotributylamine, perfluorohydrophenanthrene, or mixtures thereof. In some embodiments the composition includes the perfluorocarbon in the range of about 10 to about 70% by weight. In other embodiments, the composition also includes a handling agent. The handling agent may include saline, glycerols, polyoxamers, lecithins, or combinations thereof.

In other embodiments of the present invention, a method of making a composition for bone growth includes mixing a perfluorocarbon and DBM to form a mixture. In some embodiments, the perfluorocarbon is perfluorodecalin, perfluorohexane, perfluorotributylamine, perfluorohydrophenanthrene, or mixtures thereof. In some embodiments the composition includes the perfluorocarbon in the range of about 10 to about 70% by weight. In other embodiments, the composition also includes a handling agent. The handling agent may include glycerols, polyoxamers, lecithins, or combinations thereof.

DETAILED DESCRIPTION

Figure 1:
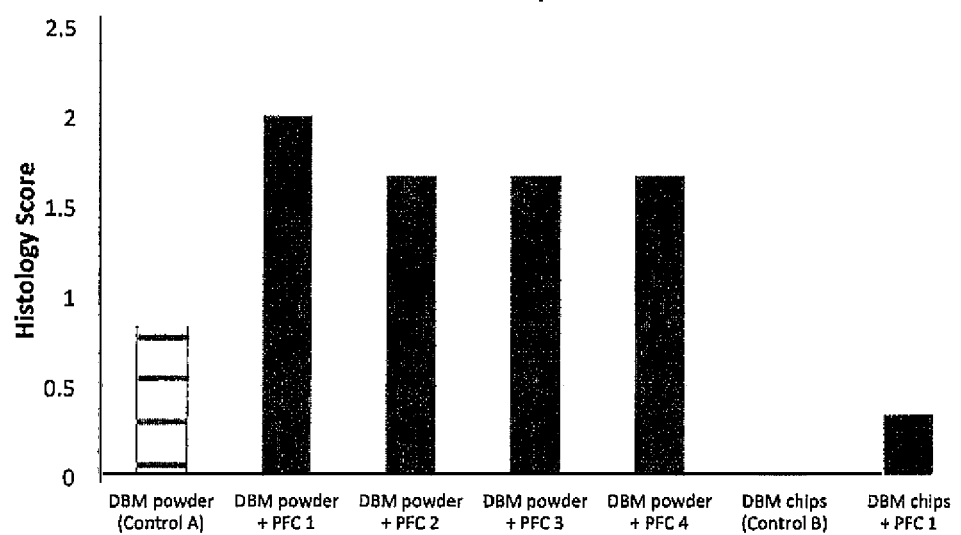
FIG. 1 is a graph of the histology scores of bone growth, 28 days after subcutaneous implantation of DBM powder alone (striped bar), DBM chips alone (striped bar), DBM powder with PFC 1, PFC2, PFC3, or PFC4 (solid bars) or DBM chips with PFC1 (solid bar), as indicated, and described in Example 1, according to one or more embodiments.

An improved composition for inducing bone growth is provided that is a combination of at least DBM and an oxygen carrier. Implantation of a composition of DBM and an oxygen carrier results in enhancement of bone formation compared to DBM alone. That is, after intramuscular and subcutaneous implantation, bone formation was found to be greater after injection of a composition of the present invention comprising DBM and an oxygen carrier (e.g. a perfluorocarbon) than a composition of DBM alone (e.g., DBM in phosphate buffered saline (PBS)). In particular, DBM and a perfluorocarbon such as perfluorodecalin, perfluorohexane, perfluorotributylamine (PFTBA), or perfluoroperhydrophenanthrene shows improved bone growth compared to DBM alone.

DBM of various forms which are suitable for implantation can be used in combination with an oxygen carrier. The various forms of commercially available DBM include powder, putty, gel, strips, paste, sheets, circular grafts, fibers, and matrices. Examples of matrices includes any DBM matrix including a three dimensional DBM matrix, such as a cancellous DBM sponge. The amount of DBM to be used ranges from approximately 0.5 ml (cubic centimeters, cc) to approximately 10 mls (ccs) depending on the site of the subject requiring bone formation. The form of DBM to use depends on the application, as will be apparent to one skilled in the art. Methodologies and uses of the various forms of DBM are disclosed in the following: Martin et al., *Spine*, 24:637-645, 1999; Khan et al., *J. Am Acad. Orthop. Surg.*, 13: 12-137, 2005; Peterson et al. *J of Bone and Joint Surg.*, 86-A, No. 10, October 2004; Sassard et al., *Orthopedics*, 23:1059-1064, 2000; Louis-Ugbo et al., *Spine*, 29:360-366, discussion Z1, 2004; Cammisa et al., *Spine*, 29:660-666, 2004, the entire contents of which are herein incorporated by reference.

Examples of oxygen carriers include, but are not limited to, perfluorocarbon-based oxygen carriers (abbreviated herein as PFC). Examples of PFCs include, but are not limited to perfluorodecalin, perfluorohexane, perfluorotributylamine [PFTBA; $(C_4F_9)_3N$], perfluorohydrophenanthrene, perfluorooctylbromide [PFOB; $C_8F_{17}Br$] (Khattak, S. F. et al., *Biotechnol. Bioeng.* 96: 156-166, 2007), and perfluoro-n-octaine (Perfluoron®). Additional examples of perfluorocarbon-based oxygen carriers include, but are not limited to, octafluoropropane, perfluorodichlorooctane, perfluorodecane, perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, and mixtures thereof. Oxygen carrier refers to a molecule capable of transporting, delivering and/or supplying oxygen to impart viability, proliferation, and differentiation to surrounding cells.

In one embodiment, the amount of oxygen carrier in the DBM composition ranges from approximately 5% to approximately 60% (w/v) (Kimelman-Bleich et al., *Biomaterials*, 30:4639-4648, 2009; Keipert, In: *Art. Cells Blood Subst. Immob Biotech*, 23, 281-394, 1995; Keipert, *Blood Substitutes*, R. W. Winslow, Academic Press, London, p. 312, 2005). In one embodiment, perfluorodecalin, perfluorohexane, perfluorohydrophenanthrene, or PFTBA are used as the oxygen carrier in a range of approximately 32-48% by weight with DBM. The amount of oxygen carrier can vary depending on the specific oxygen carrier used, as disclosed in Gomes and Gomes, "Perfluorocarbon Compounds Used As Oxygen Carriers: From Liquid Ventilation to Blood Substitutes," 2007, the entire contents of which are herein incorporated by reference.

The composition and method of the present invention may be applied to any subject having a condition that requires or would be improved with enhanced or induced bone formation.

Subjects that may require bone formation by administration of the composition of the present invention include animals, such as humans, in need of bone growth.

The term "implanting" refers to administering the composition of the present invention to a target site by methods known in the art. Known methodologies for implanting are disclosed, for example, see Martin et al., *Spine*, 24:637-645, 1999; Khan et al., *J. Am Acad. Orthop. Surg.*, 13: 12-137, 2005; Peterson et al. *J of Bone and Joint Surg.*, 86-A, No. 10, October 2004; Sassard et al., *Orthopedics*, 23:1059-1064, 2000; Louis-Ugbo et al., *Spine*, 29:360-366, discussion Z1, 2004; Cammisa et al, *Spine*, 29:660-666, 2004.

Perfluorocarbons are extremely hydrophobic viscous liquids and thus formulation of them into materials suitable for implantation into patients is challenging. They cannot be simply mixed into a hydrophilic putty or gel, thus making incorporation into materials that will form biologically compatible materials difficult. Perfluorocarbons are immiscible in these materials.

It has been found that addition of a perfluorocarbon directly to lyophilized DBM powder or granules allows the perfluorocarbon to coat the surface of the granules. In this manner a significant quantity (e.g., up to 48% by weight) of perfluorocarbon may be incorporated.

In some embodiments, the DBM and oxygen carrier composition of the present invention may be supplemented by a handling agent. A handling agent may have a greater effect when the DBM is in the form of a powder, granules or fiber. It has been found that following coating of the DBM powder with perfluorocarbon the addition of a hydrophilic handling agent may improve the handling characteristics of the oxygenated DBM composition. Non-limiting examples of handling agents include: saline, glycerols, polyoxamers, lecithins, or combinations thereof.

The DBM and oxygen carrier composition of the present invention may be supplemented with at least one of the following: bone chips (autologous or allograft), growth factors, fibrin, collagen, synthetic scaffolds, and bone marrow-derived stem cells (e.g. hematopoietic, stromal, and mesenchymal stem cells).

Growth factors, such as those in the transforming growth factor beta (TGFβ) superfamily, are known for their ability to induce bone formation in ectopic and orthotropic sites. Members of the TGFβ superfamily include BMP-2, BMP-6, BMP-7, and BMP-9, which have been shown to induce osteogenic differentiation (Kang et al., 2004, *Gene Ther.*, 11:1312-1320).

Methods for the addition of fibrin, collagen, synthetic scaffolds, and bone marrow-derived stem cells are known in the art and described in US 2009/0214649 of which paragraphs 0072-0082; 0100-0111; and 0168 are herein incorporated by reference.

The induction of bone growth using DBM and an oxygen carrier was previously disclosed in U.S. Publication Application No. 2012/0082704, the entire contents of which are herein incorporated by reference. In order to investigate the properties of a perfluorocarbon (PFC) oxygen carrier and to investigate the effects of DBM and a PFC in two environments having different vascularization, four different PFCs were assayed in combination with DBM. Specifically perfluorohexane, (PFC1), perfluorodecalin (PFC2), perfluorotributylamine (PFC3), and perfluoroperhydrophenanthrene (PFC4) were mixed with DBM (powder or chips) to form a DBM/PFC mixture. In some embodiments, the amount of PFC in the PFC/DBM mixture is in the range of about 32-48 weight %. Sterile saline was then added to provide a slurry with the handling characteristics of wet sand. This slurry was not made into an emulsion, yet still possessed adequate handling characteristics for implantation. This DBM/PFC slurry mixture was then applied to a subcutaneous pouch and an intramuscular pouch in the rat biceps femoris. A list of the PFCs and the corresponding boiling point in degrees Celsius (DC) are shown in Table 1.

TABLE 1

| Sample | Name | Boiling Point (C.) |
|---|---|---|
| PFC1 | Perfluorohexane | 56 |
| PFC2 | Perfluorodecalin | 140-143 |
| PFC3 | Perfluorotributylamine | 178 |
| PFC4 | Perfluoroperhydrophenanthrene | 215 |

Figure 2:
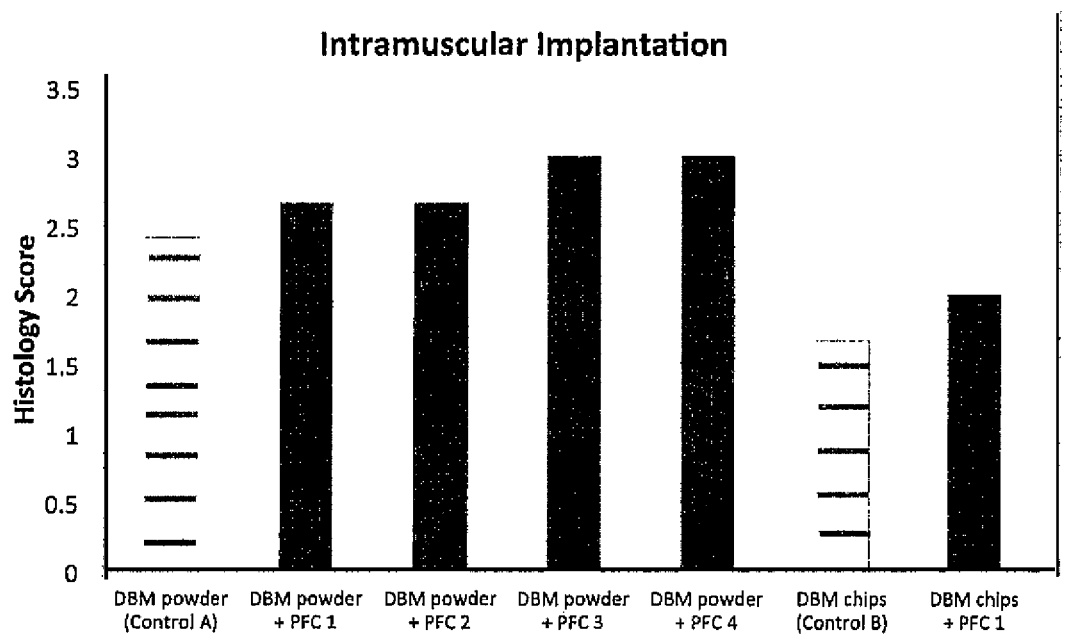
FIG. 2 is a graph of the histology scores of bone growth, 28 days after intramuscular implantation of DBM powder alone (striped bar), DBM chips alone (striped bar), DBM powder with PFC 1, PFC2, PFC3, or PFC4 (solid bars) or DBM chips with PFC1 (solid bar), as indicated, and as described in Example 1, according to one or more embodiments.

FIG. 1 shows a graph of the histology scores for bone formation following subcutaneous implantation after 28 days, and FIG. 2 shows a graph of the histology score for bone formation following intramuscular implantation after 28 days. The DBM/PFC slurry mixture treatments are shown in solid bars versus the control in striped bars. Each animal was its own control via implant of DBM alone in the contralateral limb.

In the subcutaneous implant, the DBM/PFC slurry mixture improved the amount of bone in 100% of the rat test subjects and resulted in a statistically significantly ($p<0.05$) higher histologic grade for amount of new bone formation compared to DBM alone. With the use of a commercially available DBM-chip product, no new bone formation was observed unless combined with a PFC. These results support the effectiveness of PFCs in promoting bone formation even in a challenging biologic environment. Furthermore, the results show bone formation using a non-emulsified slurry consisting essentially of DBM powder and a PFC in saline (the DBM/PFC slurry mixture). As used herein, with respect to the composition, "consisting essentially of" refers to the composition including a source of DBM and a PFC that is not emulsified. That is, the DBM/PFC mixture may include other materials that do not materially affect the characteristics imparted by the DBM and PFC, such as the amount of PFC that can be combined with the DBM in the range of about 32-48% by weight. Other characteristics of a mixture consisting essentially of DBM and PFC include the amount of bone growth induced upon implantation. That is the composition consisting essentially of DBM and PFC may include other materials as long as the other materials do not decrease the amount of bone growth compared to the bone growth resulting from a composition of only DBM and PFC. Moreover, the DBM and PFC mixture according to embodiments of the present invention does not require the addition of supplemental oxygen.

FIGS. 1 and 2 show that more new bone formation was seen in the intramuscular as compared to subcutaneous sites. In the biceps femoris intramuscular pocket, the addition of the DBM/PFC slurry mixture resulted in an increased histologic grade of new bone formation as compared to DBM alone for all the PFCs tested (e.g., PFC1, PFC2, PFC3, and PFC4), as shown in FIG. 2. This is likely attributed to the relative lack of vascularization in the subcutaneous tissues as compared to the intramuscular tissues. Nonetheless, despite the lack of vascularization in the subcutaneous tissues, new bone formation was observed, as shown in FIG. 1. Accordingly, the addition of a perfluorocarbon artificial oxygen carrier to a DBM bone void filler resulted in more new bone formation than DBM bone void filler alone, without the application of supplemental oxygen ($O_2$).

In other embodiments, a handling agent is added to the DBM/PFC mixture. The handling agent helps to improve handling characteristics of the DBM/PFC mixture which may increase the handling characteristics of the composition. For example, with the addition of a handling agent, the DBM/PFC composition may be less likely to adhere to surgical gloves. Non-limiting examples of handling agents include: saline, glycerols, polyoxamers, lecithins, and combinations thereof. A handling agent may be used as an emulsifier; however, the DBM/PFC mixture is not emulsified and is not formed into an emulsion.

EXAMPLES

Example 1

Implantation of PFC1-4 and DBM 0.4 ml of the perfluorocarbon was filtered through a 0.2 micron filter and added to 0.8 g of DBM (powder or chips) at the time of surgery prior to implantation in either a subcutaneous or an intramuscular pouch in the rat biceps femoris. Using a sterile spatula the mixture was gently mixed to ensure complete wetting out of the DBM powder. This was assessed visually. 1.4 ml of sterile saline was then added to the mixture and the resultant slurry was loaded into a 1 ml syringe with its end removed, resulting in a composition including PFC at about 32 to about 48% by weight. The mixture was lightly tamped and using the plunger on the syringe a 0.2 ml implant volume was defined. This was then introduced into the rat pouch. The PFCs included several perfluoroperhydrophenanthrene and perfluorodecalin that have achieved FDA clearance for use in various procedures in humans. In prior studies bone forms readily in DBM implanted in the SD mouse model, and thus a human DBM was selected specifically to be from low activity level batches (1965 picograms/gram BMP2; Spec>2300) (Allosource®, Centennial, Colo.). A formulation consisting of DBM+PFC+Saline was prepared at the time of surgery. Table 1 shows the PFCs used and their respective boiling points. Perfluorohexane, (PFC1), perfluorodecalin (PFC2), and perfluoroperhydrophenanthrene (PFC4) were obtained from a GMP manufacturer and have varying levels of US Device/Drug usage. Accordingly, perfluorohexane, (PFC1), perfluorodecalin (PFC2), and perfluoroperhydrophenanthrene (PFC4) represent material and supplier suitable for use in a commercial product.

30 SD Rats (Rattusnorvegicus, CR; NIH-RNU) received bilateral placement of test article (i.e., the DBM and PFC slurry) intramuscularly within the biceps femoris muscle or subcutaneously. Each animal acted as its own control with a saline/DBM implant in the contralateral limb. 0.2 cc of test article was inserted per leg. There were 5 groups of 6 rats per group (3 intramuscular, 3 subcutaneous). The study concluded at the 28 day time point at which time histology was performed following the criteria outlined in Table 2.

TABLE 2

| Estimated Percent Of Cross-Sectional Area Under Review | Histologic Criteria For Evidence Of Osteoinduction: |
|---|---|
| 0 No evidence of new bone formation. | Presence of chondroblasts/chondrocytes |
| 1 Greater than 0% up to 25% of field shows evidence of new bone formation. | Presence of osteoblasts/osteocytes |
| 2 26-50% of field shows evidence of new bone formation. | Presence of cartilage/osteoid |
| 3 51-75% of field shows evidence of new bone formation. | Presence of new bone |
| 4 76-100% of field shows evidence of new bone formation. | Presence of bone marrow |

The addition of all of the perfluorocarbon study materials implanted in a subcutaneous pocket resulted in an increased histologic grade of new bone formation as compared to DBM alone. Perfluorohexane (PFC1), perfluorotributylamine (PFTBA) (PFC3), and perfluroperhydrophenanthrene (PFC4) performed equally, while perfluorodecalin (PFC2) performed better than PFC1, PFC3, and PFC4 because perfluorodecalin it is not retained in the liver. In general, straight chain perfluorocarbons are less like likely to be toxic compared to cyclic perfluorocarbons because of the low retention time of strain chain perfluorocarbons in the liver, as described in Clark et al., 1973, *Adv. Exp. Med. Biol.* 37:687-692 and Clark et al., 1975, *Fed. Proc.,* 34:1468-1477.

As disclosed throughout and evidenced by, for example, in FIGS. 1 and 2, a composition including DBM and a PFC in a mixture, results in bone growth after implantation.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A non-emulsified composition, consisting of:
demineralized bone matrix (DBM) powder, granules and/or fibers coated with a perfluorocarbon; and
optionally consisting of a handling agent selected from the group consisting of saline, glycerols, polyoxamers, lecithins, and combinations thereof.

2. The non-emulsified composition of claim 1, wherein the perfluorocarbon has a boiling point at or within the range of about 50° C. to about 250° C.

3. The non-emulsified composition of claim 1, wherein the perfluorocarbon has a boiling point at or within the range of about 140° C. to about 145° C.

4. The non-emulsified composition of claim 1, wherein the perfluorocarbon is selected from the group consisting of perfluorodecalin, perfluorohexane, perfluoroperhydrophenanthrene, perfluorobutylamine (PFTBA), perfluorooctylbromide (PFOB), perfluoro-n-octane, octafluoropropane, perfluorodichlorooctane, perfluorodecane, perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, and mixtures thereof.

5. The non-emulsified composition of claim 1, wherein the perfluorocarbon is perfluorodecalin, perfluorohexane, perfluorobutylamine, perfluoroperhydrophenanthrene, or mixtures thereof.

6. The non-emulsified composition of claim 1, wherein the perfluorocarbon is perfluorodecalin.

7. The non-emulsified composition of claim 1, wherein the perfluorocarbon is in an amount greater than 5% (w/w) based on the total weight of the perfluorocarbon and the DBM combined.

8. The non-emulsified composition of claim 1, wherein the perfluorocarbon is in an amount from about 10 to about 70% by weight based on the total weight of the perfluorocarbon and the DBM combined.

9. The non-emulsified composition of claim 1, wherein the perfluorocarbon is in an amount from about 32 to about 48% by weight based on the total weight of the perfluorocarbon and the DBM combined.

10. The non-emulsified composition of claim 1 used for enhancing bone growth.

11. The non-emulsified composition of claim 1, wherein the DBM is in the form of powder and/or granules.

12. The non-emulsified composition of claim 11, wherein the DBM is in the form of fibers.

13. A method of making a non-emulsified composition for bone growth, the method consisting of:

coating a perfluorocarbon on DBM powder, granules, and/or fibers to form a non-emulsified mixture; and optionally adding a handling agent to the non-emulsified mixture, the handling agent being selected from the group consisting of saline, glycerols, polyoxamers, lecithins, and combinations thereof.

14. The method of claim 13, wherein the perfluorocarbon has a boiling point at or within the range of about 50° C. to about 250° C.

15. The method of claim 13, wherein the perfluorocarbon is selected from the group consisting of perfluorodecalin, perfluorohexane, perfluoroperhydrophenanthrene, perfluorobutylamine (PFTBA), perfluorooctylbromide (PFOB), perfluoro-n-octane, octafluoropropane, perfluorodichlorooctane, perfluorodecane, perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, and mixtures thereof.

16. The method of claim 13, wherein the perfluorocarbon is perfluorodecalin.

17. The method of claim 13, wherein the perfluorodecalin is in an amount greater than 5% (w/w) based on the total weight of the non-emulsified mixture.

18. The method of claim 13, wherein the DBM is in the form of powder and/or granules.

19. The method of claim 13, wherein the DBM is in the form of fibers.

* * * * *